United States Patent [19]
Karim et al.

[11] Patent Number: 6,143,928
[45] Date of Patent: Nov. 7, 2000

[54] CATALYSTS FOR LOW TEMPERATURE SELECTIVE OXIDATION OF PROPYLENE, METHODS OF MAKING AND USING THE SAME

[75] Inventors: Khalid Karim, Manchester, United Kingdom; Yajnavalkya Subrai Bhat, Riyadh, Saudi Arabia; Syed Irshad Zaheer, Riyadh, Saudi Arabia; Abdullah Bin Nafisa, Riyadh, Saudi Arabia

[73] Assignee: Saudi Basic Industries Corporation, Saudi Arabia

[21] Appl. No.: 09/131,949

[22] Filed: Aug. 10, 1998

[51] Int. Cl.[7] .................. C07C 51/16; C07C 51/235; B01J 23/00; B01J 23/72; B01J 23/42

[52] U.S. Cl. .................. 562/534; 562/535; 502/303; 502/305; 502/311; 502/312; 502/313; 502/318; 502/319; 502/321; 502/331; 502/339; 502/345; 502/353; 502/244; 502/245; 502/247; 502/248; 502/255; 502/256; 502/262; 502/263

[58] Field of Search .................. 502/303, 305, 502/311–313, 318, 319, 321, 331, 339, 345, 353, 178, 244, 245, 247, 248, 255, 256, 262, 263; 562/534, 535

[56] References Cited

U.S. PATENT DOCUMENTS

| | | | |
|---|---|---|---|
| 4,107,204 | 8/1978 | Murib | 562/534 |
| 4,126,580 | 11/1978 | Lauder | 502/303 |
| 4,250,054 | 2/1981 | Shaw et al. | 502/209 |
| 4,259,211 | 3/1981 | Krabetz et al. | 502/178 |
| 4,711,870 | 12/1987 | Yamada et al. | 502/303 |
| 4,801,568 | 1/1989 | Brazdil, Jr. et al. | 502/209 |
| 4,808,563 | 2/1989 | Velenyi | 502/241 |
| 5,077,434 | 12/1991 | Sarumaru et al. | 562/534 |
| 5,198,403 | 3/1993 | Brand et al. | 502/204 |
| 5,218,146 | 6/1993 | Takata et al. | 562/535 |
| 5,231,214 | 7/1993 | Ushikubo et al. | 558/319 |
| 5,364,825 | 11/1994 | Neumann et al. | 502/311 |
| 5,447,705 | 9/1995 | Petit et al. | 423/418.2 |
| 5,686,373 | 11/1997 | Tenten et al. | 502/312 |
| 5,759,947 | 6/1998 | Zhou | 502/324 |
| 5,780,664 | 7/1998 | Aoki | 558/323 |
| 5,808,143 | 9/1998 | Karrer et al. | 562/407 |
| 5,885,922 | 3/1999 | Hibst et al. | 502/305 |

FOREIGN PATENT DOCUMENTS

| | | |
|---|---|---|
| 0 145 467 A2 | 6/1985 | European Pat. Off. . |
| 0 293 224 A1 | 11/1988 | European Pat. Off. . |
| 0 512 846 | 11/1992 | European Pat. Off. ...... C07C 253/24 |
| 0 630 879 A1 | 12/1994 | European Pat. Off. . |

*Primary Examiner*—Mark L. Bell
*Assistant Examiner*—Patricia L. Hailey
*Attorney, Agent, or Firm*—William J. Spatz; John E. Boyd

[57] ABSTRACT

A mixed metal oxide catalytic system consisting of molybdenum, vanadium, palladium, lanthanum, niobium and X, wherein X is copper and/or chromium, providing higher yields of acrylic acid and acrolein in the low temperature oxidation of propylene with a molecular oxygen-containing gas without the production of side products such as CO.

48 Claims, No Drawings

CATALYSTS FOR LOW TEMPERATURE SELECTIVE OXIDATION OF PROPYLENE, METHODS OF MAKING AND USING THE SAME

BACKGROUND OF THE INVENTION

1. Field of Invention

The invention relates to a mixed metal oxide catalytic system for the selective oxidation of propylene to acrylic acid and acrolein. The novel catalytic system contains molybdenum, vanadium, palladium, lanthanum, niobium, and X, where X is copper, chromium or mixtures thereof. The novel catalytic system provides higher yields of acrylic acid and acrolein in the low temperature oxidation of propylene with molecular oxygen-containing gas without the production of side products such as CO. The invention also relates to methods of making and using the catalytic systems.

2. Description of Related Art

Several publications are referenced in this application. These references describe the state of the art to which this invention pertains, and are hereby incorporated by reference.

The catalytic vapor phase oxidation of propylene for the production of acrylic acid in two stages is known in the art. The first stage reaction converts propylene to mainly acrolein. The second stage converts acrolein to mainly acrylic acid. Attempts of improving the process conditions in the first stage have focused on the following drawbacks:

i. Increases in the propylene content in the feed gas being limited because of the heat of reaction. Particularly, when the reaction is carried out at higher temperatures.

ii. The reaction system must be protected from the danger of explosion at higher reaction temperatures.

iii. The selectivity to useful oxidation products is not enhanced when the reaction is carried out at higher temperatures because some of the propylene feed converts through total oxidation to products such as carbon dioxide and water.

Under these circumstances, various studies have been directed to improving the reaction conditions of these processes. U.S. Pat. No. 5,218,146 relates to a process for the production of acrylic acid by a two stage catalytic vapor phase oxidation of propylene with molecular oxygen. The first stage involves the oxidation of propylene to mainly acrolein, which comprises supplying to the first stage of the reaction a mixture containing propylene, molecular oxygen, propane, carbon dioxide, carbon monoxide and steam and using a MoFeB mixed metal oxide catalyst. The reaction temperature is in the range of 250 to 450° C., the preferred range is 320–335° C. →T 40–60° C. was observed in the reactor. Thus the highest temperature observed in the reactor may go up to as high as 400° C. This reaction temperature is quite high for any oxidation reaction requiring close control of operational parameters, particularly close control of the concentration of oxygen and propylene.

European Patent 0 630 879 A1 relates to a process for producing an unsaturated aldehyde and an unsaturated acid which comprises subjecting propylene to gas phase catalytic oxidation with molecular oxygen in the presence of a catalyst comprising a composite oxide of the formula $Mo_aBi_bFe_cA_dB_eC_fD_gO_x$ at 310° C., wherein: A represents nickel and/or cobalt; B represents at least one element selected from phosphorus, boron, arsenic, tellurium, tungsten, antimony and silicon; and D represents at least one element selected from potassium, rubidium, cesium and thallium; and wherein a, b, c, d, e, f, g and x represent, respectively, the number of atoms of Mo, Bi, Fe, A, B, C, D and O, and where a is 12, $0<b\leq10$, $0<c\leq10$, $1\leq d\leq10$, $0\leq e\leq10$, $0\leq f\leq10$ and $0<g\leq2$ and x has a value dependent on the oxidation state of the respective elements. At a conversion of 80.5%, a selectively of 90.2% for acrolein and acrylic acid was reported.

European Patent 0 293 224 A1 relates to a process for the production of acrolein from propylene using the catalyst $Mo_aW_bBi_cFe_dA_eB_fC_gD_hO_x$, wherein A is an element selected from the group consisting of nickel and cobalt; B is at least one element selected from the group consisting of alkali metals, alkaline earth metals and thallium; C is at least one element selected from the group consisting of phosphorus, arsenic, boron and niobium; and D is at least one element selected from the group consisting of silicon, aluminum and titanium and the subscripts a, b, c, d, e, f, g, h and x are respectively the number of atoms of the elements Mo, W, Bi, Fe, A, B, C, D and O, provided that a=2 to 10, b=0 to 10, on condition that a+b=12, c=0.1 to 10, d=0.1 to 10, e=2 to 20, f=0.005 to 3.0, g=0 to 4, h=0.5 to 15 and x is a number required to satisfy the valence requirements of the other elements. The reaction temperature was 330° C.

Another European Patent 0 145 467 A3 relates to the catalytic oxidation of olefins to α, B unsaturated carboxylic acids and aldehydes at a temperature in the range 65–80° C., but carried out at a high pressure in the range 71 to 168 psi. Moreover, the method was operated in liquid phase in batch mode. At the end of 4 hours, a 31.0 g/l catalyst yield of acrylic acid was obtained. This system has several disadvantages such as requiring a batch mode operation, a high pressure liquid phase reaction, catalyst recovery, activation, etc.

None of the prior art has disclosed or suggested the advantages of the catalysts disclosed in present invention which provide high performance for selective production of acrylic acid and acrolein through a gas phase partial oxidation process of propylene with zero or insignificant production of carbon monoxide at low temperatures.

Accordingly, it would be desirable to produce an improved catalyst for use in the selective production of acrylic acid and acrolein without the production of carbon monoxide.

OBJECTS OF THE INVENTION

It is an object of the invention to overcome the above-identified deficiencies.

It is another object of the invention to provide an improved catalytic system for the low temperature selective oxidation of propylene.

It is a further object of the invention to provide an improved catalyst for the single stage low temperature oxidation of propylene to acrylic acid and acrolein.

It is a still further object of the invention to provide methods of making and using the improved catalytic system.

The foregoing and other objects and advantages of the invention will be set forth in or be apparent from the following description.

SUMMARY OF THE INVENTION

As described in the present invention, the ability to lower the reaction temperatures for propylene oxidation in vapor phase under a continuous mode and yet provide very high yields of acrolein and acrylic acid together is surprisingly achieved using the catalyst of the invention. The catalysts disclosed in the present invention are designed in such a way that a single catalyst provides dual functions of activation of propylene to acrolein and further oxidation of acrolein to acrylic acid.

More specifically, the invention relates to a catalyst system for use in a method where propylene is oxidized with molecular oxygen to acrylic acid and acrolein in a gas phase reaction with high selectivity at temperatures of from 150° C. to 450° C. and at pressures of from 1–50 bar. This is achieved using a catalyst with a calcined composition of $Mo_aV_bLa_cPd_dNb_eX_f$ wherein: X=Cu or Cr or both;

a is 1;

b is 0.01 to 0.9;

c is >0 to 0.2, preferably 0.0000001 to 0.2;

d is 0.0000001 to 0.2;

e is 0 to 0.2, preferably 0.0000001 to 0.2; and f is 0 to 0.2, preferably 0.0000001 to 0.2.

The numerical values of a, b, c, d, e, and f represent the relative gram-atom ratios of the elements Mo, V, La, Pd, Nb and X respectively, in the catalyst. The elements are present in combination with oxygen, preferably in the form of various oxides. The composition can also be described as $Mo_aV_bLa_cPd_dNb_eX_fO_y$, where y is a number required to satisfy the valence requirements of the other elements.

The invention also relates to a selective low temperature catalytic process for the production of acrolein or acrylic acid or both by the vapor phase oxidation of propylene. The catalytic process of the invention does not produce carbon monoxide which is not environmentally friendly and which can have a significant impact on down stream separation costs.

Other objects as well as aspects, features and advantages of the present invention will become apparent from a study of the present specification, including the claims and specific examples.

DESCRIPTION OF THE PREFERRED EMBODIMENTS

One aspect of the invention relates to an improved catalytic system for the selective oxidation of propylene. The catalysts of the invention can be used with or without a support. Suitable supports for the catalysts include alumina, silica, titania, zirconia, zeolites, silicon carbide, Mo Carbide, molecular sieves and other microporous/nonporous/mesoporous materials, and mixtures thereof. When used on a support, the supported catalyst usually comprises from about 10 to 50% by weight of the catalyst composition, with the remainder being the support material.

Another aspect of the invention relates to methods of making the improved catalysts. The choice of the compounds used as well as the specific procedures followed in preparing a catalyst can have a significant effect on the performance of a catalyst. Preferably, the elements of the catalyst composition are in combination with oxygen as oxides.

According to one embodiment, the catalyst is prepared from a solution of soluble compounds (salts, complexes or other compounds) of each of the metals. The solution is preferably an aqueous system having a pH of 1 to 10 and more preferably a pH of 1 to 7, and a temperature of from about 30° C. to about 100° C. Generally, a mixture of compounds containing the elements is prepared by dissolving sufficient quantities of the soluble compounds and dispersing the insoluble compounds so as to provide desired gram-atom ratios of the elements in the catalyst composition. The catalyst composition is then prepared by removing the water and/or other solvent from the mixture of the compounds in the solution system. The dried catalyst is calcined by heating to a temperature from about 250° C. to about 450° C. in air or oxygen for a period of time from about one hour to about 16 hours to produce the desired catalyst composition.

Preferably, the molybdenum is introduced into the solution in the form of ammonium salts such as ammonium paramolybdate, or organic acid salts of molybdenum such as acetates, oxalates, mandelates, and glycolates. Some other partially water soluble molybdenum compounds which may be used include molybdenum oxides, molybdic acid, and chlorides of molybdenum.

Preferably, the vanadium is introduced into the solution in the form of ammonium salts such as ammonium metavanadate and ammonium decavanadate, or organic salts of vanadium such as acetates, oxalates, and tartrates. Partially water soluble vanadium compounds such as vanadium oxides, and sulfates of vanadium can also be used. To achieve complete solubility, an amount of oxalic or tartaric acid can be added.

Preferably, the lanthanum is introduced into the catalyst slurry in the form of salts of La such as oxides, acetates, chlorides, nitrates, etc.

Preferably, the palladium is introduced into the catalyst slurry in the form of Pd on activated charcoal or alumina or a solution of salts of palladium such as acetates, chlorides, nitrates, etc.

Preferably, the copper is introduced into the catalyst slurry in the form of salts of copper such as oxides, acetates, chlorides, nitrates, etc.

Preferably, the chromium is introduced into the catalyst slurry in the form of salts of chromium such as oxides, acetates, chlorides, nitrates, etc.

Preferably, the niobium is used in the form of oxalates or hydrate oxides. Other sources of this metal in soluble form include compounds in which the metal is coordinated, bonded or complexed to a beta-diketonate, carboxylic acid, and amine, and alcohol, or an alkanolamine.

According to one embodiment, the catalyst is prepared by the following general procedure. Aqueous solutions of vanadium and molybdenum are prepared separately. The vanadium solution is mixed with the molybdenum solution at a specified temperature and pH to form a gel solution. The rest of the required components are slowly added to the combined gel solution. After mixing and heating for about ½ to 2 hours, the resultant gel is dried to incipient wetness with continuous stirring at about 100° C.

After drying the resultant gel mixture at 120° C. for 16 hours, the catalyst is heated to 350° C. at the rate of 2° per minute and calcined at this temperature in air for 4 hours to produce the desired oxide composition. This regime seems to be close to optimum as it provides a catalyst with the desired structure and properties.

Another aspect of the invention relates to methods of using the catalyst system of the invention. More specifically, the invention relates to an improved method for the oxidation of propylene. The raw material used as the source of the propylene can be a gas stream which contains at least three volume percent of propylene or mixtures of propylene and propane. The gas stream can also contain minor amounts of $C_2$ or $C_4$ alkanes and alkenes, with less than thirty volume percent of each. The gas stream can also contain major amounts, more than five volume percent, of nitrogen/argon, carbon dioxide, and water in the form of steam.

The reaction mixture in carrying out the process is generally one mole of propylene, 0.01 to 2.0 moles of molecular oxygen, either as pure oxygen or in the form of air, and zero to 4.0 moles of water in the form of steam. Molecular oxygen sources for the feed include, purified oxygen, air and oxygen enriched air depending on the economics of separation and the hydrocarbon conversion achieved. The ratio of propylene to oxygen varies with the desired conversion and the selectivity of the catalyst, but generally is in the range of 1/5–5/1. Reaction can also be effected especially in the presence of diluents such as argon, nitrogen or steam. The ratio of propylene to diluents can be in the range 1/5–1/1. The water vapor or steam may be used as a reaction diluent and as a heat moderator for the reaction and may also act as desorption accelerators of the reaction product in the vapor phase oxidation reaction. Other gases may be used as reaction diluents or heat moderators such as helium, nitrogen, and carbon dioxide.

Accordingly, the gaseous components of the reaction mixture include propylene, oxygen and diluents, and these components are uniformly admixed prior to being introduced into the reaction zone. The components may be preheated, individually or after being admixed, prior to being introduced into the reaction zone which should have a temperature of from about 150° C. to about 450° C.

The reaction zone generally has a pressure of from 1 to 50 bar, preferably from 1 to 30 bar; a temperature of from about 150° C. to about 450° C., preferably from 200° C. to 300° C.; a contact time between the reaction mixture and the catalyst of from about 0.01 seconds to 100 seconds, preferably from 0.1 seconds to 10 seconds; and a space hourly velocity of from about 50 to about 50,000 $h^{-1}$, preferably from 100 to 10,000 $h^{-1}$ and most preferably from 200 to 3,000 $h^{-1}$.

The contact time is defined as the ratio between the apparent volume of the catalyst bed and the volume of the gaseous reaction mixture feed to the catalyst bed under the given reaction conditions in a unit of time.

The space velocity is calculated by determining total reactor outlet gas equivalent in liters of the total effluent evolved over a period of one hour divided by the liters of catalyst in the reactor. This room temperature volume is converted to the volume at 0° C. at 1 bar.

The reaction pressure is initially provided by the feed of the gaseous reactants and diluents and after the reaction has commenced, may be maintained by the use of a suitable back-pressure controller placed on the reactor outlet stream.

The reaction temperature is provided by placing the catalyst bed within a tubular converter having walls which is placed in a furnace heated to the desired reaction temperature.

The oxygen concentration in the feed gas mixture can vary widely, from 0.1 to 50% or higher of the feed mixture by applying proper measures to avoid explosion problems. Air is the preferred source of oxygen in the feed. The amount of oxygen present may be a stoichiometric amount, or lower, of the hydrocarbons in the feed.

The process is generally carried out in a single stage with all the oxygen and reactants being supplied as a single feed with non-reacted initial reactants being recycled. However, multiple stage addition of oxygen or hydrocarbon to the reactor can be used or recycling of un-reacted gases with purge mode can be applied to improve the overall productivity or yield of the desired products.

The liquid products of the reaction can be separated from the unreacted feed hydrocarbons by condensation or scrubbing, usually by water or dilute acid.

The methods of using the catalyst of the invention are not limited to the oxidation of propylene to acrylic acid and acrolein. The catalyst may also be used for oxidizing alpha-beta unsaturated aliphatic aldehydes in the vapor phase with molecular oxygen to produce the corresponding alpha-beta unsaturated carboxylic acids such as meth-acrylic acid and meth-acrolein from iso-butane.

EXAMPLES

The following examples are illustrative of some of the products and methods of making the same falling within the scope of the present invention. They are, of course, not to be considered in any way limitative of the invention. Numerous changes and modifications can be made with respect to the invention.

The catalyst samples prepared in the examples were evaluated using the following method.

Catalyst Testing

Catalyst evaluations were carried out in a stainless steel fixed bed tubular reactor under standard process conditions. The gas feed compositions used for the evaluation of the catalysts contained propylene, propane, oxygen, water, $CO_2$ and argon in the mole ratio of 20:10:10:10:20:30, respectively. Reactions were carried out at a temperature of 206° C., a pressure of 15 psia and at a space velocity of about 1,090 $h^{-1}$ using 11 cc of calcined catalyst.

Reaction products were analyzed on-line by gas chromatography. Oxygen, argon and carbon monoxide were analyzed using a 2.5 m by 3 mm column of 13× molecular sieve. Carbon dioxide, propane and propylene were analyzed using a 2 m by 3mm column packed with material sold under the trade name HAYESEP Q. Liquid products (acrylic acid, acrolein, acetic acid and water) were collected for a certain period in the cold trap and were analyzed using a 2 m by 3mm column packed with material sold under the trademark PORAPAK QS. In all cases, the conversion and selectively calculations were based on the stoichiometry.

Example 1

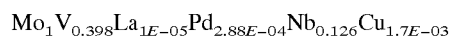

$Mo_1V_{0.398}La_{1E-05}Pd_{2.88E-04}Nb_{0.126}Cu_{1.7E-03}$

Ammonium metavanadate (Aldrich Chemicals, Assay= 99.0%) in the amount of 7.6 grams was added to 80 ml of distilled water and heated to 90° C. with stirring. A yellow color solution with a pH between 5 and 6 was obtained (Solution A). 3.4 grams of niobium hydrate oxide (80% $Nb_2O_5$, Niobium Products Company, USA) and 20 grams of oxalic acid were added to 80 ml of water and heated to 95° C. with continuous stirring to give a clear white color solution with a pH of 0.57 (Solution B). Solutions A and B were mixed together at 90° C. with continuous stirring of the content of the mixture. Color changes from pale yellow-brown-green-dark green were observed. The pH of the solution was 1.20 at 85° C. 8 g of oxalic acid was added very slowly to the above solution with continuous stirring of the contents of the mixture at 90° C. A dark blue-green color solution with a pH of 0.86 at 86° C. was obtained (Solution C).

Ammonium paramolybdate tetra hydrated (Aldrich Chemicals A.C.S-12054-85-2) in the amount of 28.8 grams was added to 30 ml of water and heated to 60° C. to give a colorless solution with a pH between 5.0 and 6.0 (Solution D). Solution D was then slowly combined with Solution C to give dark blue to dark gray color precipitates (Mixture E).

The required amount of palladium followed by cupric oxide and lanthanum nitrate was slowly added to the gel mixture. This dark color combination was stirred vigorously to achieve a homogeneous gel mixture which was then slowly dried to incipient dryness with continuous stirring.

The resulting solid was placed in a China dish and dried additionally in an oven at 120° C. for sixteen hours. The dried material was cooled to room temperature and placed in a furnace. The temperature was raised from room temperature to 350° C. at the rate of 2°/min and thereafter held at 350° C. for four hours.

The calcined catalyst was formulated into uniform 40–60 mesh size particles and evaluated for the propylene oxidation reaction. At a reaction temperature of 206° C., the reaction product showed a 94.51% recycled yield to acrylic acid and acrolein (acrylic acid 19.81% and acrolein 80.17%) and a balance of acetic acid and $CO_2$. At 250° C., the reaction product showed a 77% selectivity to acrylic acid and acrolein (acrylic acid 79% and acrolein 21%) and a balance of acetic acid and $CO_2$.

Example 2

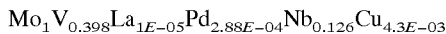
$Mo_1V_{0.398}La_{1E-05}Pd_{2.88E-04}Nb_{0.126}Cu_{4.3E-03}$

The procedure was the same as Example 1 except 0.05 gm of cupric oxide was used. At a reaction temperature of 206° C., the reaction product showed a 95.10% recycled yield to acrylic acid and acrolein (acrylic acid 16% and acrolein 84%) and a balance of acetic acid and $CO_2$.

Example 3

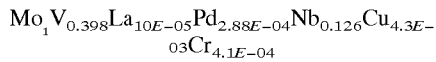
$Mo_1V_{0.398}La_{10E-05}Pd_{2.88E-04}Nb_{0.126}Cu_{4.3E-03}Cr_{4.1E-04}$ The procedure was the same as Example 2 followed by the addition of 0.242 g of ammonium dichromate. At a reaction temperature of 206° C., the reaction product showed a 92.65% recycled yield to acrylic acid and acrolein (acrylic acid 34% and acrolein 66%) and a balance of acetic acid and $CO_2$.

Example 4

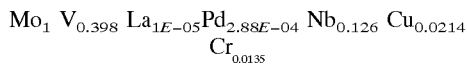
$Mo_1\ V_{0.398}\ La_{1E-05}Pd_{2.88E-04}\ Nb_{0.126}\ Cu_{0.0214}\ Cr_{0.0135}$ The procedure was the same as Example 1 except 0.8 g of ammonium dichromate and 0.25g of cupric oxide was added. At a reaction temperature of 206° C., the reaction product showed a 96.11% recycled yield to acrylic acid and acrolein (acrylic acid 22% and acrolein 78%) and a balance of acetic acid and $CO_2$.

Example 5

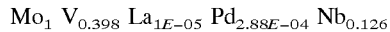
$Mo_1\ V_{0.398}\ La_{1E-05}\ Pd_{2.88E-04}\ Nb_{0.126}$

The procedure was the same with Example 1 except cupric oxide was not added. At a reaction temperature of 206° C., the reaction products showed a 95.10% recycled yield to acrylic acid and acrolein (acrylic acid 15% and acrolein 85%). The balance was acetic acid and $CO_2$.

The BET surface area for the catalysts described in the examples varied from 20 to 35 $m^2/g$. The catalysts of the present invention showed an optimum redox behavior resulting in a high activity and highly selectivity towards the partial oxidation products. Based on catalytic data, the following general characteristics can be concluded for the catalysts of the invention:

1. The catalyst system shows high selectivity to acrylic acid and acrolein at low temperatures in a single stage reaction.
2. Oxidation of propylene shows a lower →T of 10–15° C. Lower →T can have positive impact on the reactor design.
3. Low temperature oxidation of propylene over the catalysts disclosed in the present invention does not produce carbon monoxide as a side product.
4. Relative selectivity to acrylic acid and acrolein depends on the catalyst composition, reaction temperature, space velocity, pressure and feed composition.

The above description of the invention is intended to be illustrative and not limiting. Various changes or modifications in the embodiments described may occur to those skilled in the art. These can be made without departing from the spirit or scope of the invention.

What is claimed is:

1. A catalyst for selective oxidation of propylene to acrylic acid and acrolein containing a catalyst composition comprising the elements Mo, V, La, Pd, Nb, X, and oxygen and having the following formula:

$Mo_aV_bLa_cPd_dNb_eX_fO_y;$ wherein X=Cu or Cr or mixtures thereof;

a is 1;

b is 0.01 to 0.9;

c is >0 to 0.2;

d is 0.0000001 to 0.2;

e is 0.0000001 to 0.2;

f is 0.0000001 to 0.2; and wherein the numerical values of a, b, c, d, e, and f represent the relative gram-atom ratios of the elements Mo, V, La, Pd, Nb, and X, respectively, in the catalyst and y is a number required to satisfy the valence requirements of the elements Mo, V, La, Pd, Nb, and X.

2. The catalyst of claim 1, wherein said catalyst is a supported catalyst comprising a support.

3. The catalyst of claim 2, wherein the said support is selected from the group consisting of alumina, silica, titania, zirconia, silicon carbide, Mo-carbide and zeolites.

4. The catalyst of claim 2, wherein the said support is selected from the group consisting of molecular sieves, microporous materials, nanoporous materials, mesoporous materials and combinations thereof.

5. The catalyst of claim 2, wherein said supported catalyst comprises from 5 to 50% by weight catalyst composition and 50 to 95% by weight support.

6. A single stage catalytic process for direct conversion of propylene to acrylic acid and acrolein by means of propylene oxidation comprising the step of oxidizing of propylene in a reaction mixture comprising propylene and oxygen or a compound capable of providing oxygen in a reaction zone in the presence of the catalyst of claim 1.

7. The process of claim 6, wherein said catalyst is in the form of a fixed bed and said oxidation is carried out by introducing a feed mixture comprising propylene into the reaction zone.

8. The process of claim 7, wherein said feed mixture further comprises air or oxygen.

9. The process of claim 7, wherein said feed mixture comprises molecular oxygen ranging from 0.1 to 50% by volume of the feed.

10. The process of claim 7, wherein said feed mixture is diluted with steam in an amount ranging from 0 to 60% by volume.

11. The process of claim 6, wherein said catalyst is in the form of a fluidized bed and said oxidation is carried out by introducing a feed mixture comprising propylene into reaction zone.

12. The process of claim 6, wherein oxidation is achieved while operating in gas phase at a temperature of from 100 to 450° C., under a pressure of from 1 to 50 bars, and with a contact time between the reaction mixture and the catalyst of from 0.1 to 10 seconds.

13. The process of claim 6, wherein said oxidation provides at least a 98% recycled yield of acrylic acid and acrolein at low temperature in the reaction zone.

14. The process of claim 6, wherein said oxidation of propylene produces no CO as a by-product using molecular oxygen with a range from 0.1 to 50% of the feed.

15. The process of claim 6, further comprising introducing oxygen into the feed mixture in multi-steps to increase the yield, selectivity or both yield and selectivity of desired products.

16. The process of claim 6, wherein said step of oxidizing propylene provides at least a 90% recycled yield to acrylic acid and acrolein with at least 15% acrylic acid and at least 75% acrolein.

17. The process of claim 6, wherein said step of oxidizing propylene provides at least a 75% selectivity to acrylic acid and acrolein, with at least 70% acrylic acid and at least 15% acrolein.

18. The process of claim 6, wherein said step of oxidizing propylene provides at least a 96% recycled yield to acrylic acid and acrolein with at least 22% acrylic acid and at least 78% acrolein.

19. The process of claim 6, wherein said step of oxidizing propylene provides at least a 77% selectivity to acrylic acid and acrolein, with at least 79% acrylic acid and at least 21% acrolein.

20. A single stage catalytic process for direct conversion of propylene to acrylic acid and acrolein comprising the step of oxidizing propylene in a single stage in the presence of the catalyst of claim 1.

21. A process for performing a catalytic chemical reaction in fluid phase comprising contacting at least one reactant in fluid phase under suitable reaction conditions with a catalyst system containing the catalyst of claim 1.

22. The process of claim 21, wherein said catalytic chemical reaction converts one or more fluid phase reactants to one or more fluid phase products.

23. The process of claim 22, wherein said one or more fluid phase reactants comprise propylene and said one or more fluid phase products comprise acrylic acid, acrolein and acetic acid.

24. The process of claim 22, wherein said one or more fluid phase reactants comprise alpha-beta unsaturated aliphatic aldehydes and oxygen and said one or more fluid phase products comprise alpha-beta unsaturated carboxylic acids.

25. The process of claim 21, wherein said catalytic chemical reaction oxidizes lower alkanes to corresponding acids.

26. A process for performing a catalytic chemical reaction comprising the step of introducing a reactant in fluid phase into a reaction zone containing the catalyst of claim 1.

27. A process of forming the catalyst of claim 1, comprising the steps of:
a) forming a mixture containing Mo, V, La, Pd, Nb and X in a solution;

b) drying said mixture to form solid material; and
c) calcining said dried solid material to form said catalyst.

28. The process of claim 27, wherein said mixture is an aqueous system having pH from 1 to 10.

29. The process of claim 28, wherein said mixture is an aqueous system having pH from 1 to 7.

30. The process of claim 27, wherein said mixture is formed by combining a first solution with a second solution, wherein said first solution and said second solution each contain at least one element from the group consisting of Mo, V, Nb, La, Cr, Cu and Pd.

31. The process of claim 27, wherein said calcining comprises heating said dried solid material to a calcining temperature of about 250 to 450° C. in air or oxygen for a period of time from about one hour to about 16 hours.

32. The catalyst of claim 1, wherein said catalyst composition consists essentially of the elements Mo, V, La, Pd, Nb, X, and oxygen.

33. The catalyst of claim 1, wherein X is Cu.

34. The catalyst of claim 1, wherein X is Cr.

35. A catalyst for selective oxidation of propylene to acrylic acid and acrolein, said catalyst containing Mo, V, La, Pd, Nb, X, and oxygen, made by a process comprising the steps of:
a) combining the elements Mo, V, La, Pd, Nb, and X, in the following ratio, to form a mixture:
$Mo_a V_b La_c Pd_d Nb_e X_f$
wherein: X=Cu or Cr or both;
a is 1;
b is 0.01 to 0.9;
c is >0 to 0.2;
d is 0.0000001 to 0.2;
e is 0.0000001 to 0.2; and
f is 0.0000001 to 0.2; and
b) calcining said mixture to form said catalyst containing Mo, V, La, Pd, Nb, X, and oxygen.

36. The catalyst of claim 35, wherein said catalyst is a supported catalyst comprising a support.

37. The catalyst of claim 35, wherein X is Cu.

38. The catalyst of claim 35, wherein X is Cr.

39. A single stage catalytic process for direct conversion of propylene to acrylic acid and acrolein compromising the step of oxidizing propylene in a single stage in the presence of the catalyst of claim 35.

40. A process for performing a catalytic chemical reaction in fluid phase comprising contacting at least one reactant in fluid phase under suitable reaction conditions with a catalyst system containing the catalyst of claim 35.

41. A catalyst composition having the following formula:

$$Mo_a V_b La_c Pd_d Nb_e X_f O_y;$$

wherein X=Cu or Cr or mixtures thereof;
a is 1;
b is 0.01 to 0.9;
c is >0 to 0.2;
d is 0.0000001 to 0.2;
e is 0.0000001 to 0.2; and
f is 0.0000001 to 0.2; and
wherein the numerical values of a, b, c, d, e, and f represent the relative gram-atom ratios of the elements Mo, V, La, Pd, Nb, and X, respectively, in the catalyst and y is a number required to satisfy the valence requirements of the elements Mo, V, La, Pd, Nb, and X.

42. The catalyst of claim 41, wherein X is Cu.

43. The catalyst of claim 41, wherein X is Cr.

44. A process for performing a catalytic chemical reaction in fluid phase comprising contacting at least one reactant in fluid phase under suitable reaction conditions with a catalyst system containing the catalyst of claim 41.

45. A catalyst containing Mo, V, La, Pd, Nb, X, and oxygen made by a process comprising the steps of:
 a) forming a mixture consisting essentially of the elements Mo, V, La, Pd, Nb, and X in the following ratio:

$$Mo_a V_b La_c Pd_d Nb_e X_f$$

wherein: X=Cu or Cr or both;
 a is 1;
 b is 0.01 to 0.9;
 c is >0 to 0.2;
 d is 0.0000001 to 0.2;
 e is 0.0000001 to 0.2; and
 f is 0.0000001 to 0.2; and
 b) calcining said mixture to form said catalyst containing Mo, V, La, Pd, Nb, X, and oxygen.

46. The catalyst of claim 45, wherein X is Cu.

47. The catalyst of claim 45, wherein X is Cr.

48. A process for performing a catalytic chemical reaction in fluid phase comprising contacting at least one reactant in fluid phase under suitable reaction conditions with a catalyst system containing the catalyst of claim 45.

* * * * *